US012082925B2

(12) United States Patent
Lee et al.

(10) Patent No.: US 12,082,925 B2
(45) Date of Patent: Sep. 10, 2024

(54) SELF-REFERENCE POINT SETTING TYPE BLOOD COMPONENT MEASURING METHOD AND APPARATUS

(71) Applicant: Korea Electronics Technology Institute, Seongnam-si (KR)

(72) Inventors: Sung Chul Lee, Yongin-si (KR); Cheol Koo Hahn, Gyeonggi-do (KR); Won Ki Park, Suwon-si (KR)

(73) Assignee: Korea Electronics Technology Institute, Seongnam-si (KR)

( * ) Notice: Subject to any disclaimer, the term of this patent is extended or adjusted under 35 U.S.C. 154(b) by 737 days.

(21) Appl. No.: 17/137,924

(22) Filed: Dec. 30, 2020

(65) Prior Publication Data

US 2021/0196158 A1 Jul. 1, 2021

Related U.S. Application Data

(63) Continuation of application No. PCT/KR2020/002160, filed on Feb. 14, 2020.

(30) Foreign Application Priority Data

Dec. 26, 2019 (KR) .................. 10-2019-0175703

(51) Int. Cl.
*A61B 5/145* (2006.01)
*A61B 5/00* (2006.01)
*A61B 5/1455* (2006.01)

(52) U.S. Cl.
CPC ........ *A61B 5/14532* (2013.01); *A61B 5/0059* (2013.01); *A61B 5/1455* (2013.01)

(58) Field of Classification Search
CPC ........... A61B 5/14532–14552; A61B 5/14558; A61B 5/1464; A61B 5/0059; A61B 5/0064; A61B 2562/04–046
See application file for complete search history.

(56) References Cited

U.S. PATENT DOCUMENTS 5,054,487 A * 10/1991 Clarke ................ A61B 5/1455
356/407
5,725,480 A * 3/1998 Oosta ..................... A61B 5/442
600/556

(Continued)

FOREIGN PATENT DOCUMENTS

| JP | 5519534 B2 | 6/2014 |
| KR | 10-1961147 B | 3/2019 |
| KR | 10-2019-0081634 A | 7/2019 |

OTHER PUBLICATIONS

International Search Report and Written Opinion mailed Sep. 18, 2020 in International Application No. PCT/KR2020/002160, in 9 pages.

*Primary Examiner* — Benjamin S Melhus
*Assistant Examiner* — Samuel C Kim
(74) *Attorney, Agent, or Firm* — Knobbe, Martens, Olson & Bear, LLP (57) ABSTRACT

This application relates to a self-reference point setting type blood component measuring method and apparatus using light. In one aspect, the method includes applying light to a skin of a subject to be measured and setting a reference point on a surface of the skin adjacent to a point at which the light is applied. The method further includes calculating a concentration of a blood component from a light intensity measured at the reference point and a light intensity measured at another point. According to some embodiments, the accuracy and precision of measurement are increased in measuring blood in a non-invasive manner.

9 Claims, 4 Drawing Sheets

(56) References Cited

U.S. PATENT DOCUMENTS

| | | | | |
|---|---|---|---|---|
| 6,026,314 | A * | 2/2000 | Amerov | A61B 5/1455 600/316 |
| 6,405,069 | B1 * | 6/2002 | Oraevsky | A61B 90/36 600/407 |
| 10,054,594 | B2 | 8/2018 | Xu et al. | |
| 2009/0281536 | A1 * | 11/2009 | Beckman | A61B 5/0059 606/41 |
| 2010/0004522 | A1 * | 1/2010 | Varela | A61B 5/150503 600/347 |
| 2012/0010477 | A1 * | 1/2012 | Amano | G01N 21/359 356/342 |
| 2014/0012103 | A1 * | 1/2014 | Nishida | A61B 5/1455 600/316 |
| 2016/0242682 | A1 | 8/2016 | Gulati et al. | |
| 2016/0317070 | A1 * | 11/2016 | Sivaraman | A61B 5/7282 |
| 2018/0160908 | A1 * | 6/2018 | Kim | A61B 5/0095 |
| 2018/0199871 | A1 * | 7/2018 | Pauley | A61B 5/14552 |
| 2020/0163596 | A1 * | 5/2020 | Sanyal | A61B 5/14532 |

\* cited by examiner

SELF-REFERENCE POINT SETTING TYPE BLOOD COMPONENT MEASURING METHOD AND APPARATUS

CROSS REFERENCE TO RELATED APPLICATIONS

This is a continuation application of International Patent Application No. PCT/KR2020/002160, filed on Feb. 14, 2020, which claims priority to Korean Patent Application No. 10-2019-0175703 filed on Dec. 26, 2019, contents of both of which are incorporated herein by reference in their entireties.

BACKGROUND

Technical Field

The described technology relates to a technique in which microcomponents (e.g., blood sugar or glucose) in blood are measured by a non-invasive method using light.

Description of Related Technology

Currently, as a representative method of testing blood components such as blood sugar (glucose) and the like in blood, there are invasive methods in which a blood sample is taken, and blood components are measured using a dedicated tester. The invasive method causes psychological instability, consumes time for testing, and causes discomfort in patients who need to check blood, such as blood sugar at all times.

SUMMARY

The described technology is directed to providing a method and apparatus for measuring blood in which the accuracy and precision of measurement are increased in measuring blood in a non-invasive manner in order to improve the psychological stability of patients who need to check blood levels, such as blood sugar, at all times and to reduce consumption of time for testing and relieve discomfort.

One aspect of the described technology provides a method of measuring a blood component by setting a self-reference point for each individual subject to be measured in order to establish a reference point for removing signal displacement irrelevant to a blood component to be measured according to an influence of the subject to be measured, a measurement position, and an environment, and the like in optical non-invasive measurement of blood components such as blood sugar, etc.

Specifically, according to the described technology, the reference point is recognized and set on a surface of skin of each subject to be measured using a one-dimensional linear image sensor, and a concentration of the blood component such as blood sugar is calculated from an intensity of light measured at the reference point and an intensity of light measured at another point.

A principle of the recognition of the reference point is as follows. Light incident to the skin proceeds through processes such as reflection, refraction, absorption, and scattering from various body components such as an epidermis, a corium, and subcutaneous fat, and the like. Some of the light is re-reflected to the outside of a body only through the epidermis. The light reflected only through the epidermis does not include information about the blood component. Therefore, when the light is selectively measured and used as a reference for light refracted through paths such as the corium, the subcutaneous fat, and the like, it is possible to accurately measure a blood component based on a self-reference point of the subject to be measured rather than a separate reference value.

In the calculation of the concentration of the blood component based on the self-reference point, a formula for calculating an intensity of the light at the reference point and a formula for calculating an intensity of light at a point other than the reference point may be used. The concentration of the blood component may be calculated by inverse calculation from known variables included in the formulas and from variables that are a function of a concentration of a blood component in a corium.

Obtaining of optical signals (reference signals) at an epidermal reference point and main signals at the other corium and subcutaneous fat other than the epidermis and measuring the blood component in an optical non-invasive method using the obtained optical signals may be performed using, for example, a light-receiving element in which photodiode (PD) cells are arranged in one or more dimensions.

The spirit of the described technology described above will be clearly understood through specific embodiments described below with reference to the accompanying drawings.

According to the described technology, the following effects can be obtained. When a blood component is measured in an optical non-invasive manner, the precision and accuracy of a measuring device can be improved by securing a reference irrelevant to conditions of skin of an individual person (e.g., a color, a thickness, a degree of contamination, presence of body hair, and the like). It is possible to significantly reduce a calibration process of the measuring device according to characteristic of the individual person. Skin reflection or noise caused by a blood component irrelevant to a subject to be measured can be canceled, and thus the number of necessary light sources can be reduced. With miniaturization of a device and simplification of an algorithm for deriving a blood component from measured data, it is possible to make a module optimal for implementing a wearable device.

BRIEF DESCRIPTION OF THE DRAWINGS

FIGS. 1A and 1B illustrate a light pattern appearing on a surface of skin by scattering of light applied to the skin, wherein FIG. 1A is a plan view and FIG. 1B is a cross-sectional view.

DETAILED DESCRIPTION

In order to solve problems of invasive methods, non-invasive methods of measuring a blood have been developed. Among non-invasive blood test techniques, techniques using light are currently reported as a variety of products, and recently, techniques in which oxygen saturation, a pulse rate, and the like are measured using light-emitting diodes (LEDs) of mobile phones have been developed.

As a representative non-invasive detector, a detection method using an infrared light is disclosed in the paper. Here, data, which is obtained by optically measuring the light transmitted through skin after infrared wavelengths that react with glucose in blood is irradiated to the blood, is corrected with data for blood sugar measured in an invasive method (i.e., by a previously proven measuring method). The above method is implemented with an optical module using one photodiode and a plurality of LEDs.

However, the optical non-invasive blood analyzer has the following problems. It is difficult to set a reference point with respect to measured values because reflective characteristics of light depend on conditions of skin of an individual person (e.g., color, thickness, degree of contamination, presence of body hair, etc.). Furthermore, it is difficult to secure precision thereof due to various optical attenuation and noise sources which are present inside a human body such as an epidermis, subcutaneous fat, etc.

Therefore, in order to measure only components related to blood sugar from skin characteristics of each individual person who uses a blood sugar measuring device and from various microcomponents present in a body, it is necessary to introduce an appropriate reference in consideration of the above problems. For this reason, currently, by non-invasive products using light, tests for other components such as blood sugar, urea, and the like, except for simple tests for oxygen saturation, a pulse rate, and the like, are hardly performed. High-precision optical blood analyzers using continuous light sources such as a halogen lamp have also been developed. However, the high-precision optical blood analyzers require expensive parts such as a spectrum analyzer and are not suitable for personal use or as wearable devices because a size of a measuring device is large.

Therefore, the development of techniques and devices, which may be miniaturized to be used as wearable devices, implemented at a low cost for individual personalized health care, and implemented within an allowable range as medical devices by reducing an error in measured values, is a very important issue in the field of optical non-invasive blood component analyzers.

Advantages and features of the described technology and methods of achieving the same will be clearly understood with reference to the accompanying drawings and embodiments described in detail below. However, the described technology is not limited to the embodiments to be disclosed below but may be implemented in various different forms. The embodiments are provided in order to fully explain the present embodiments and fully explain the scope of the described technology for those skilled in the art. The scope of the described technology is only defined by the appended claims. Meanwhile, the terms used herein are provided only to describe the embodiments of the described technology and not for purposes of limitation. In this specification, the singular forms include the plural forms unless the context clearly indicates otherwise. It will be understood that the terms "comprise" and/or "comprising," when used herein, specify some stated components, steps, operations and/or elements, but do not preclude the presence or addition of one or more other components, steps, operations and/or elements.

Hereinafter, exemplary embodiments of the described technology will be described in detail with reference to the accompanying drawings. When reference numerals are assigned to components of each drawing, it should be noted that, even when the same components are illustrated in different drawings, the same numerals are assigned to the same components whenever possible. In addition, in descriptions of the described technology, when detailed descriptions of related well-known technology are deemed to unnecessarily obscure the gist of the described technology, they will be omitted.

Figure 1A:
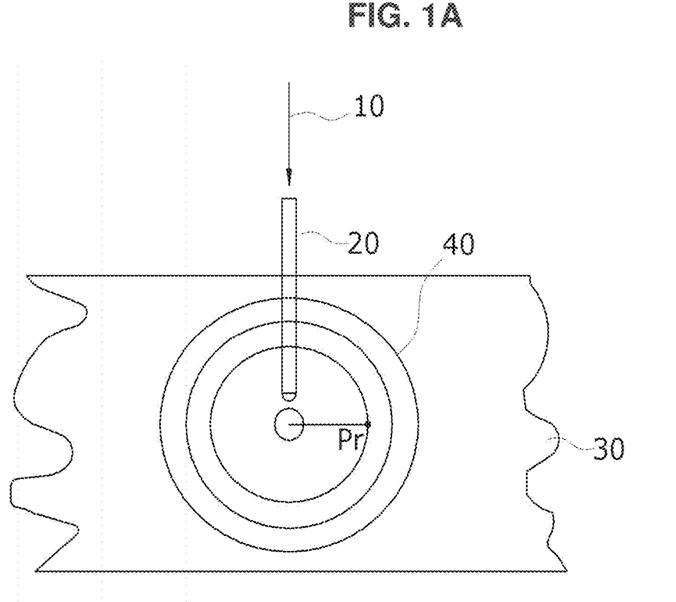
Figure 1B:
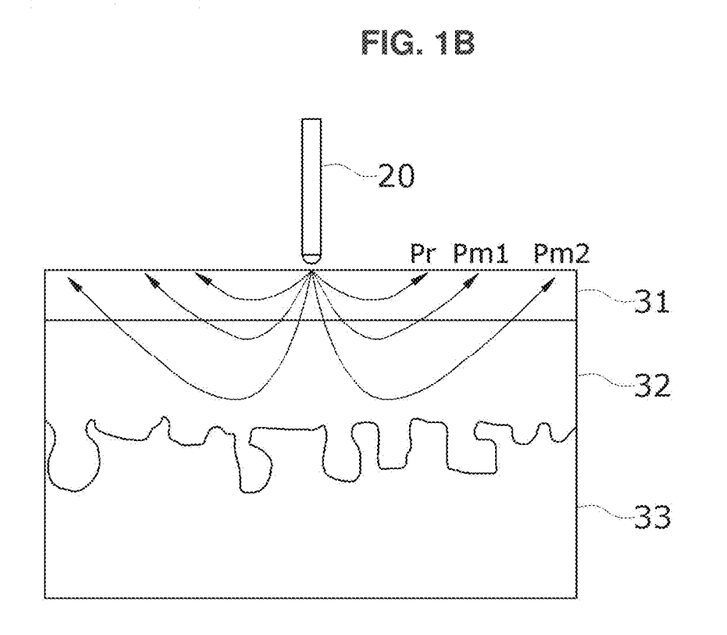

FIGS. 1A and 1B illustrate a light pattern that appears due to scattering, refraction, and the like of light applied to skin due to microcomponents (blood components) and other components in blood, wherein FIG. 1A is a plan view and FIG. 1B is a cross-sectional view.

When light emitted from a light source 10 is applied to skin 30 through an optical fiber 20, some of the applied light is absorbed, refracted, and scattered by the skin and internal components so that a light pattern 40 in the form of a concentric circle centered on a point, to which the light is applied, is generated (see FIG. 1A). The concentric light pattern 40 is generated due to a difference in absorption, refraction, and scattering of the light according to a difference in components of an epidermis 31, a corium 32, and subcutaneous fat 33.

In the epidermis 31, since a degree of light absorption and a degree of scattering are the same, a point $P_r$ independent of a blood component (e.g., blood sugar (glucose)) is present at a specific distance away from the light source on a surface of the skin. The distance to the point $P_r$ depends on a state of a subject to be measured but is usually about several millimeters (mm) radially from the light source.

After the light passes through the point $P_r$ (i.e., a maximum distance at which the light appears on the surface of the skin by being absorbed and scattered in the epidermis 31), it is absorbed and scattered in the corium 32 and the subcutaneous fat 33 and appears in a concentric pattern on the surface of the skin at points $P_{m1}$, $P_{m2}$, . . . .

By setting the point $P_r$ as a reference point and measuring a relative intensity of the absorbed and scattered light appearing at an arbitrary point $P_{mk}$ farther than the point $P_r$, the concentration of a specific blood component included in the blood can be calculated. If regression analysis using a light source having multi-wavelengths is performed, precision of the calculation may be further improved.

Hereinafter, embodiments of the described technology will be described. Here, for explanation convenience, a blood component will be limited to glucose, which is an index of blood sugar.

Figure 2:
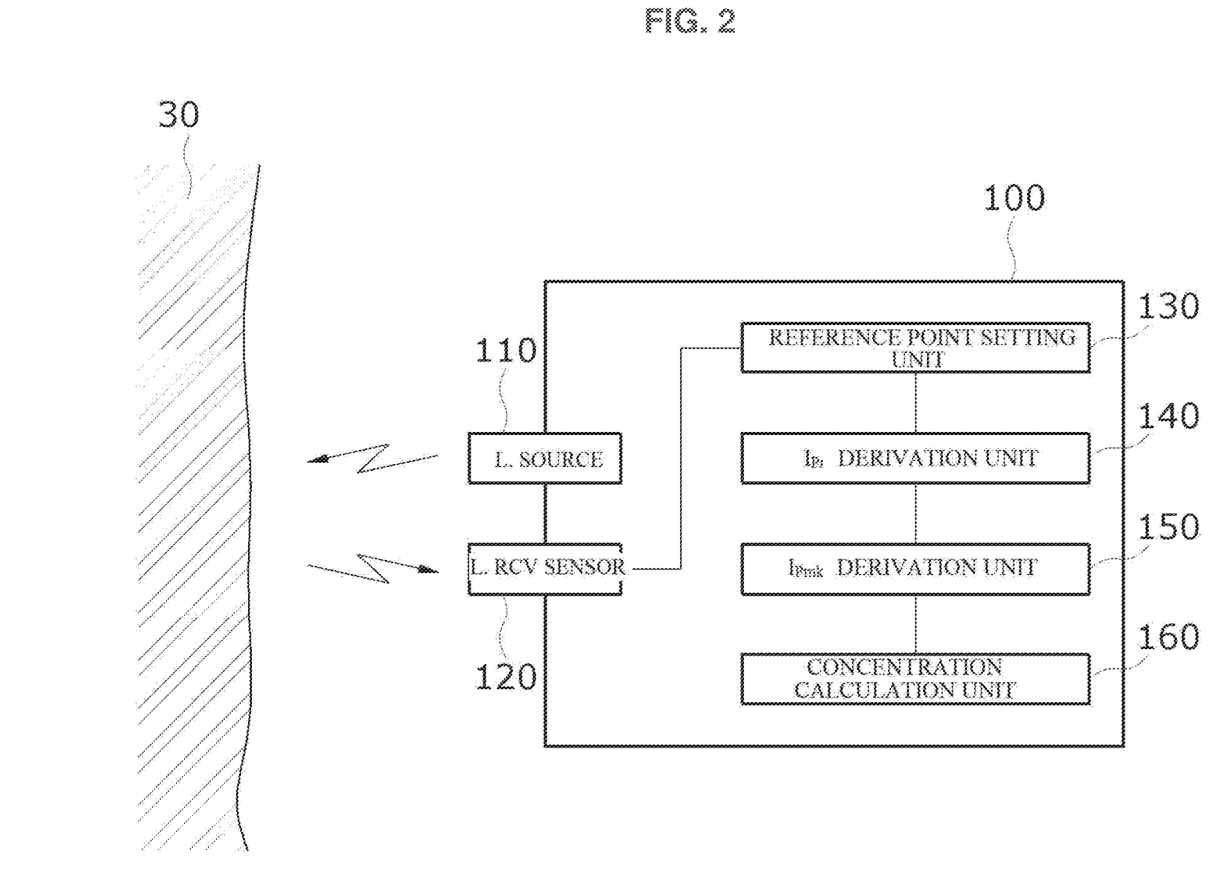
FIG. 2 is a block diagram of a blood component measuring apparatus according to an embodiment of the described technology.

FIG. 2 is a block diagram of a blood component measuring apparatus 100 according to an embodiment of the described technology. The blood component measuring apparatus 100 includes a light source 110 configured to irradiate skin 30 with light, a light-receiving sensor 120 configured to detect a light pattern appearing on a surface of the skin by absorbing, refracting, reflecting, and scattering the light irradiated to the skin 30 in the skin, a reference point setting unit (or a reference point setting processor) 130 configured to recognize a point at which the absorbed, refracted, reflected, and scattered light appears on the epidermis 31 of the skin regardless of blood components and skin components and to set the point as a reference point $P_r$, a light intensity $I_{Pr}$ derivation unit (or a light intensity $I_{Pr}$ derivation processor) 140 configured to analyze the light pattern detected by the light-receiving sensor 120 and to derive an intensity $I_{Pr}$ of the light at the reference point $P_r$, a light intensity $I_{Pmk}$ derivation unit (or a light intensity $I_{Pmk}$ derivation processor) 150 configured to analyze the light pattern detected by the light-receiving sensor 120 and to derive an intensity $I_{Pmk}$ of the light at points $P_{mk}$ (=$P_{m1}$, $P_{m2}$, . . . ) on a skin surface farther from the reference point $P_r$, and a blood component concentration calculation unit (or a blood component concentration calculation processor) 160 configured to calculate the concentration of a blood component from the derived light intensities $I_{P_r}$ and $I_{Pmk}$.

Figure 3:
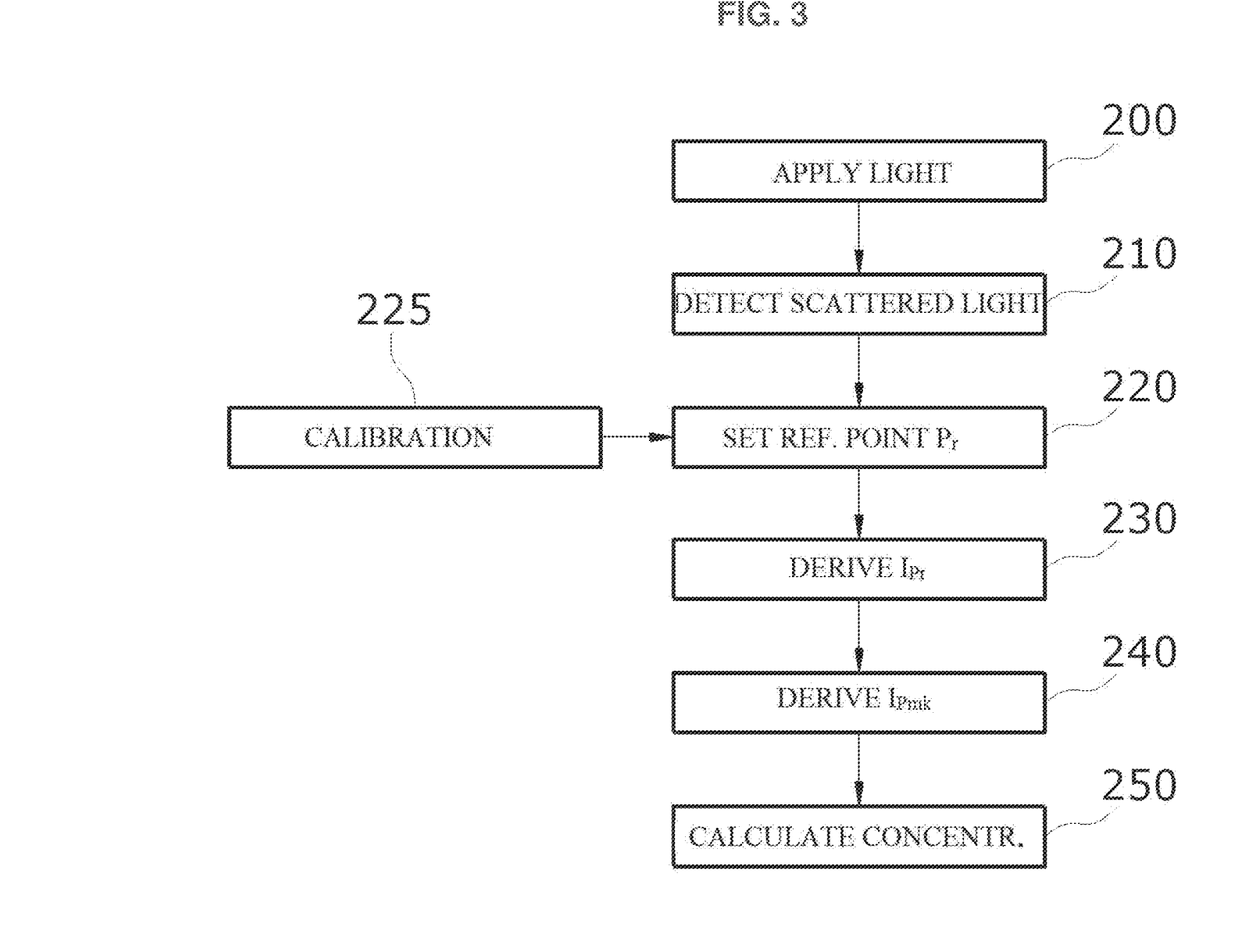
FIG. 3 is a flowchart illustrating an operation sequence of a blood component measuring method according to an embodiment of the described technology.

FIG. 3 is a flowchart illustrating an operation sequence of a blood component measuring method according to an embodiment of the described technology.

In operation 200, light emitted from a light source 110 is applied to skin 30. In this case, the light may be applied to the skin through an optical fiber.

In operation 210, using a light-receiving sensor 120, a light pattern appearing on a surface of the skin by absorbing, refracting, reflecting, and scattering the light in an epidermis, a corium, and a subcutaneous fat layer in the skin 30 is detected. Here, the light-receiving sensor can be an array in which a plurality of photodiode (PD) cells are arranged in one dimension.

In operation 220, a point on an epidermis 31 of the skin, at which the absorbed, refracted, reflected, and scattered light appears regardless of blood components and skin components, is recognized and the point is set as a reference point $P_r$.

In operation 225, a calibration process is involved for each individual person when the reference point $P_r$ is set. The calibration process is a process of determining the reference point $P_r$ through repetitive pre-tests required by entering a calibration mode in advance before executing a formal test mode for a specific individual person because the point $P_r$ is different for each blood component measuring method. In operation 230, the light pattern detected by the light-receiving sensor 120 is analyzed and a light intensity $I_{P_r}$ at the reference point $P_r$ is derived.

In operation 240, the light pattern detected by the light-receiving sensor 120 is analyzed and a light intensity $I_{Pmk}$ at points $P_{mk}(=P_{m1}, P_{m2}, \ldots)$ on a skin surface far from the reference point $P_r$ is derived.

In operation 250, a concentration of a blood component is calculated from the derived light intensity $I_{P_r}$ and the derived light intensity $I_{Pmk}$.

Each of the above operations will be described below together with an action of each component of the blood component measuring apparatus.

The light source 110 may include a plurality of individual light emitters. For example, the light source 110 may be configured to include a first light source in a wavelength band from 1,280 to 1,330 nm belonging to an infrared (IR) or near infrared (NIR) band and a second light source in another wavelength band from 1,590 to 1,650 nm. In actuality, as illustrated in FIG. 1A, the plurality of light sources 110 irradiate the surface of the skin 30 with light through the optical fiber 20 or other concentrators so that a focal diameter thereof becomes about 1 mm or less.

Figure 4:
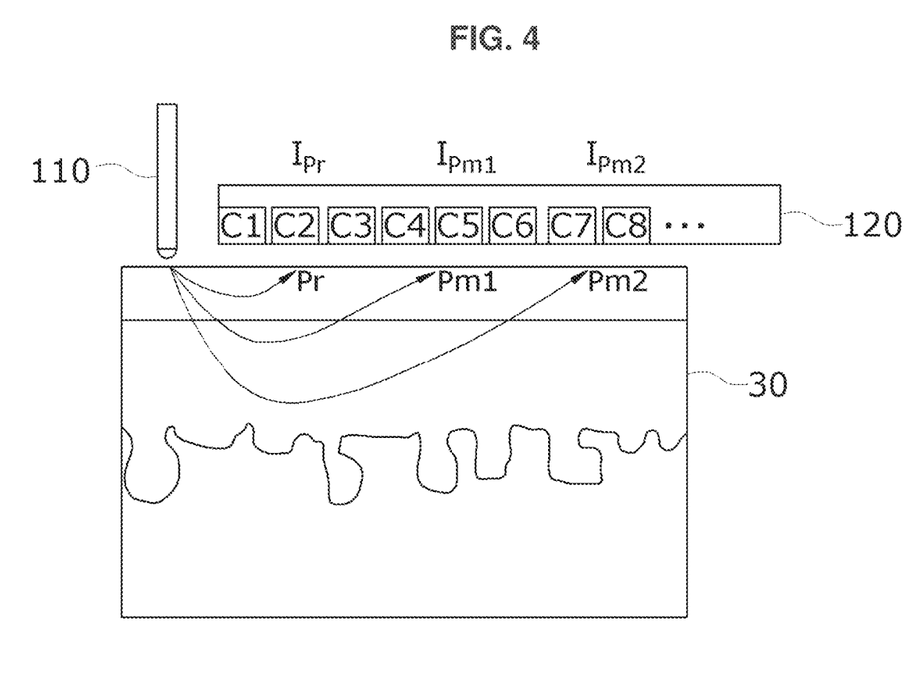
FIG. 4 is a schematic diagram of light pattern detection using a light-receiving sensor configured as a one-dimensional photodiode array.

The light-receiving sensor 120 uses a PD array in which a plurality of PD cells C1, C2, C3, . . . are arranged in at least one dimension to detect a concentric light pattern around a light irradiation point on the surface of the skin. The above process is illustrated in FIG. 4. FIG. 4 is a schematic diagram of light pattern detection using a light-receiving sensor 120 configured as a one-dimensional PD array.

A light pattern appearing on a surface of skin is detected using the light-receiving sensor 120 in the PD array type in which PD cells are radially arranged from a point at which light is applied to the surface of the skin by a light source 110 (or an optical fiber). An image processor (not illustrated) processes signals of the detected light pattern and derives a light intensity $I_{P_r}$ at a point $P_r$ and a light intensity $I_{Pmk}$ at points $P_{mk}$ by utilizing a difference in light intensity for each PD. In order to detect the light pattern in the radial distances Pr and $P_{mk}$ from the light source 110, it is sufficient that the light-receiving sensor 120 has a one-dimensional linear array. However, of the matter of course, the light-receiving sensor 120 may have a two-dimensional planar array.

Referring to FIGS. 2 and 3 again, the reference point setting unit 130 sets the reference point $P_r$ using the light pattern detected by the light-receiving sensor 120. As described above, the point $P_r$ is positioned at the epidermis 31 so that the point $P_r$ is a maximum distance point at which the light pattern is not affected by the blood components and other skin components. Various algorithms may be used to recognize the point $P_r$. For example, the point may be specified by a calibration process through repetitive measurements. Since the point $P_r$ is different for each individual person, the reference point $P_r$ may be determined through repetitive pre-tests required by executing a calibration mode in advance before executing a formal test mode for a specific individual person.

After the reference point $P_r$ is set, the light intensity her derivation unit 140 derives a light intensity $I_{P_r}$ at the set reference point from optical signals (light pattern detection signals) detected by the light-receiving sensor 120. To this end, image processing (digital signal processing) techniques or related algorithms may be used. When a pattern of the signals detected by the arranged PD cells of the light-receiving sensor 120 is input to a digital signal processor (DSP), the reference point $P_r$ may be recognized by a predetermined processing method and the light intensity $I_{P_r}$ at the reference point may be derived.

Next, the light intensity $I_{Pmk}$ derivation unit 150 that derives the light intensity at the points $P_{mk}(=P_{m1}, P_{m2}, \ldots)$ on a skin surface detects the light intensity at points $P_{mk}(=P_{m1}, P_{m2}, \ldots)$ on the skin surface beyond the reference point $P_r$ set on the surface of the skin. Even in this case, the digital signal processing techniques or related algorithms may be used, as in the case of deriving the light intensity $I_{P_r}$.

Finally, the blood component concentration calculation unit 160 calculates the concentration of the blood component (in this embodiment, 'blood sugar') from the derived light intensity $I_{P_r}$ and the derived light intensity $I_{Pmk}$. A procedure for calculating the concentration of the blood sugar is as follows.

First, the light intensity $I_{P_r}$ may be expressed as Equation 1 below.

$$I_{P_r} = I_0 \cdot \beta_e \cdot \exp(\Sigma \alpha_i l_r) \quad \text{[Equation 1]}$$

$I_{P_r}$ denotes the intensity of light at a reference point $P_r$, $I_0$ denotes the intensity of light applied to a surface of skin from a light source, $\beta_e$ denotes scattering efficiency by an epidermis, $\alpha_i$ denotes an absorption constant by each of components constituting the epidermis, and $l_r$ denotes an effective traveling path of light between the light source and the reference point $P_r$.

In addition, the light intensity $I_{Pmk}$ at the points $P_{mk}$ may be expressed as Equation 2 below.

$$I_{Pmk} = I_0 \cdot (1-\beta_e) \cdot \beta_d \cdot \exp(\Sigma(\alpha \alpha_i l_r + \alpha_j l_{mk} + \alpha_G l_{mk})) \quad \text{[Equation 2]}$$

$I_{Pmk}$ denotes the light intensity measured at a $k^{th}$ cell of the PD array, $\beta_d$ denotes scattering efficiency by a corium, a denotes a proportionality constant including a ratio of a traveling path of light from the light source to the reference point $P_r$ to a traveling path of light from the light source to the measured points $P_{mk}$, $\alpha_j$ denotes a light absorption rate by components constituting an epidermis and components excluding blood sugar among components constituting the corium, $\alpha_G$ denotes an absorption constant proportional to the concentration of the blood sugar, and $l_{mk}$ denotes an effective traveling path of the light between the light source and the measured points $P_{mk}$.

Using Equations 1 and 2, the concentration of the blood sugar, that is, the glucose, may be calculated. To this end, a ratio of the light intensity $I_{P_{mk}}$ to the light intensity $I_{P_r}$ may be expressed as Equation 3 below $$\frac{I_{P_{mk}}}{I_{P_r}} = \frac{\beta_d}{\beta_e}\exp\left(\sum((a-1)\alpha_i l_r + \alpha_j l_{mk} + a_G l_{mk})\right) + \quad [\text{Equation 3}]$$
$$\beta_d \cdot \exp\left(\sum((a-1)\alpha_i l_r + \alpha_j l_{mk} + \alpha_G l_{mk})\right)$$

Using the light intensity derived from the optical signals detected by the light-receiving sensor 120 at the plurality of points $P_{mk}$, variables defined in Equation 3 may be specified regardless of an absolute value of the intensity $I_0$ of the light emitted from the light source. When a blood sugar level is changed due to food intake or metabolic activity, the light intensity $I_{P_{mk}}$ in Equation 3 may be abbreviated as a function of $\alpha_G$. Also, the function $\alpha_G$ is a function of the concentration of the blood sugar. Therefore, as a result, a value of the concentration of the blood sugar may be derived from the above equation.

The scattering efficiencies $\beta_e$ and $\beta_d$ and the correction constant a may be obtained by a system of linear equations by substituting the values measured at the plurality of points $P_{mk}$ into Equation 3 using the PD array light-receiving sensor 120. That is, the values measured at the points $P_r$ and $P_{mk}$ are measured from the same irradiation light, and a change according to measurement conditions such as skin conditions, a degree of contamination, presence of body hair, and the like may be removed. Only a change in amount of light due to the components of the corium may be detected based on a relative intensity compared to the point (the reference point) Pr instead of an absolute value of the measured light intensity.

As described above, since a value of $I_{Pmk}/I_{Pr}$ in Equation 3 is expressed as a function of the absorption rate $\alpha_j$ by the components constituting only the corium, the number of independent variables is significantly reduced in a relationship of deriving the blood sugar on the basis of the measured light intensity, and as a result, the number of light sources required in an optical non-invasive blood sugar measuring device may be significantly reduced. Therefore, the measuring device may be miniaturized, and its precision may be improved. Furthermore, according to the above efficacy, the described technology may be easily implemented as a wearable device.

As described above, the described technology may be implemented in aspects of an apparatus or a method. In particular, the functions or processes of the respective components of the described technology may be implemented as at least one of a DSP, a processor, a controller, an application-specific integrated circuit (ASIC), a programmable logic device (e.g., a field-programmable gate array (FPGA), etc.), and other electronic elements, and as hardware elements including a combination thereof. In addition, the functions or processes may be implemented in software in combination with hardware elements or independently, and the software may be stored in a recording medium.

While the configuration of the described technology has been described in detail with reference to the exemplary embodiments, it will be understood by those skilled in the art that the described technology may be implemented in a specific form different from the contents disclosed herein without changing the technological scope or essential features. The above-described embodiments should be considered in a descriptive sense only and not for purposes of limitation. The scope of the described technology is defined not by the detailed description but by the appended claims, and encompasses all modifications and alterations derived from meanings, the scope and equivalents of the appended claims.

What is claimed is:

1. A method for measuring a blood component comprising:
   providing a light source and an optical fiber;
   arranging the light source and the optical fiber to be aligned with respect to a skin of a subject to be measured;
   emitting light by the light source;
   applying, by the optical fiber, the emitted light to the skin of the subject, while the light source and the optical fiber are aligned with respect to the skin of the subject, the optical fiber having a focal diameter in a range of 1 mm or less;
   providing a light-receiving sensor comprising a plurality of photodiodes;
   arranging the plurality of photodiodes radially from a point at which the emitted light is applied to the skin of the subject;
   detecting, by the plurality of photodiodes of the light-receiving sensor, a concentric light pattern on a surface of the skin based on at least some of the applied light being absorbed, refracted, and scattered by the skin and internal body components comprising an epidermis, a corium, and subcutaneous fat, wherein the concentric light pattern comprises a plurality of light circles having different diameters, wherein the plurality of light circles of the concentric light pattern are respectively detected by the plurality of photodiodes of the light-receiving sensor, and wherein the plurality of light circles comprise:
      a smallest light circle, closest to a center of the concentric light pattern detected by a first photodiode of the plurality of photodiodes, and
      remaining light circles larger than the smallest light circle and farther than the smallest light circle from the center of the concentric light pattern, the remaining light circles detected by remaining photodiodes of the plurality of photodiodes;
   selecting, by a reference point setting processor, a point on the smallest light circle as a reference point, wherein the reference point is defined as a maximum distance point from the center of the concentric light pattern at which the concentric light pattern is not affected by blood components and skin components other than the epidermis of the subject, and wherein selecting the reference point comprises performing a calibration process through repetitive measurements;
   analyzing, by a first light intensity derivation processor, the concentric light pattern to derive a first light intensity of the smallest light circle of the concentric light pattern;
   analyzing, by a second light intensity derivation processor, the concentric light pattern to derive second light intensities of the remaining light circles of the concentric light pattern;
   measuring an intensity of the emitted light applied to the surface of the skin; and calculating, by a blood component concentration calculation processor, a concentration of a blood component based on the derived first light intensity of the smallest light circle of the concentric light pattern and the second light intensities of the remaining light circles of the concentric light pattern based on a predetermined relationship among the intensity of the emitted light, the first light intensity, the second light intensities, and the blood components.

2. The method of claim 1, wherein the predetermined relationship comprises Equations 1-3 represented below:

$$I_{P_r} = I_0 \cdot \beta_e \cdot \exp(\Sigma \alpha_i l_r) \quad \text{[Equation 1]}$$

wherein $I_{P_r}$ denotes the first light intensity, $I_0$ denotes the intensity of the emitted light applied to the surface of the skin, wherein $\beta_e$ denotes a scattering efficiency by the epidermis, $\alpha_i$ denotes an absorption constant of each component constituting the epidermis, and $l_r$ denotes an effective traveling path of the emitted light between the light source and the reference point $P_r$, $$I_{P_{mk}} = I_0 \cdot (1-\beta_e) \cdot \beta_d \cdot \exp(\Sigma(a\alpha_i l_r + \alpha_j l_{mk} + \alpha_G l_{mk})) \quad \text{[Equation 2]}$$

wherein $I_{P_{mk}}$ denotes the second light intensities, $\beta_d$ denotes a scattering efficiency by the corium, a denotes a proportionality constant including a ratio of a traveling path of the emitted light from the light source to the reference point $P_r$ to a traveling path of the emitted light from the light source to the other points, $\alpha_j$ denotes a light absorption rate by components constituting an epidermis and components excluding blood sugar among components constituting the corium, $\alpha_G$ denotes an absorption constant proportional to the concentration of the blood sugar, and $l_{mk}$ denotes an effective traveling path of the emitted light between the light source and points $P_{mk}$, and $$\frac{I_{P_{mk}}}{I_{P_r}} = \frac{\beta_d}{\beta_e} \exp\left(\sum((a-1)\alpha_i l_r + \alpha_j l_{mk} + a_G l_{mk})\right) + \quad \text{[Equation 3]}$$

$$\beta_d \cdot \exp\left(\sum((a-1)\alpha_i l_r + \alpha_j l_{mk} + \alpha_G l_{mk})\right).$$

3. The method of claim 2, wherein the scattering efficiencies se and pa and the correction constant a are obtained by a system of linear equations.

4. The method of claim 1, wherein the light source comprises one or more light sources configured to emit light in different frequency bands.

5. The method of claim 1, wherein the light source comprises a first light source configured to emit light in a wavelength band from 1,280 nm to 1,330 nm and a second light source configured to emit light in a wavelength band from 1,590 nm to 1,650 nm.

6. The method of claim 1, wherein the calculating comprises:
calculating variables that are a function of the concentration of the blood component in the corium, using a formula for calculating the first light intensity and a formula for calculating the second light intensities.

7. A component measuring apparatus configured to perform the method of claim 1.

8. The apparatus of claim 7, wherein the light source comprises one or more light sources configured to emit light in different frequency bands.

9. The apparatus of claim 7, wherein the light source comprises a first light source configured to emit light in a wavelength band from 1,280 nm to 1,330 nm and a second light source configured to emit light in a wavelength band from 1,590 nm to 1,650 nm.

* * * * *